United States Patent
Terpay

[19]

[11] Patent Number: 5,942,893

[45] Date of Patent: Aug. 24, 1999

[54] SHIELDED EDDY CURRENT SENSOR FOR ENHANCED SENSITIVITY

[75] Inventor: Gregory Weston Terpay, Whippany, N.J.

[73] Assignee: General Dynamics Advanced Technology Systems, McLeansville, N.C.

[21] Appl. No.: 08/989,355

[22] Filed: Dec. 12, 1997

Related U.S. Application Data

[63] Continuation-in-part of application No. 08/682,066, Jul. 16, 1996, abandoned.

[51] Int. Cl.⁶ .............................. G01B 7/14; G01P 3/44; G01N 27/72; H01F 27/36

[52] U.S. Cl. ................. 324/207.18; 73/660; 324/164; 324/207.12; 324/225; 324/239; 336/84 R

[58] Field of Search .................................... 324/164, 173, 324/174, 207.12, 207.16–207.19, 207.26, 225, 232, 239–243, 262; 318/658; 73/660, 661; 340/870.32, 870.35, 870.36; 310/168; 336/84 R, 84 C, 84 M

[56] References Cited

U.S. PATENT DOCUMENTS

| | | | |
|---|---|---|---|
| 3,229,197 | 1/1966 | Renken, Jr. | 324/240 |
| 3,532,969 | 10/1970 | McCullough et al. | 324/229 |
| 3,890,516 | 6/1975 | Widdowson et al. | 318/658 X |
| 3,932,813 | 1/1976 | Gallant | 324/173 X |
| 4,234,848 | 11/1980 | Diem et al. | 324/262 |
| 4,847,556 | 7/1989 | Langley | 324/207.18 |
| 4,855,677 | 8/1989 | Clark, Jr. et al. | 324/232 X |
| 4,866,380 | 9/1989 | Meins et al. | 324/207.12 X |
| 5,264,733 | 11/1993 | Tigges | 324/207.16 X |
| 5,323,891 | 6/1994 | Waite | 324/243 |
| 5,434,504 | 7/1995 | Hollis et al. | 324/207.17 |
| 5,469,053 | 11/1995 | Laughlin | 324/207.18 |
| 5,617,024 | 4/1997 | Simpson et al. | 324/240 X |

FOREIGN PATENT DOCUMENTS

| | | | |
|---|---|---|---|
| 0053155 | 3/1991 | Japan | 324/240 |

*Primary Examiner*—Gerard Strecker
*Attorney, Agent, or Firm*—Jenner & Block

[57] ABSTRACT

An eddy current sensor comprises a generally E-shaped core having three parallel legs joined together by a bridge. Current carrying coils are mounted on each of the outer legs and a signal coil is mounted on the central leg. Identical a.c. currents are caused to flow through the two outer coils for generating two magnetic fields which combine to form a sensing magnetic field extending outwardly from the ends of the legs for sensing purposes but which cancel one another within the central leg. The sensor is disposed within an E-shaped, hollow shield of an eddy current producing, electrically conductive material. The sensor fits within the shield as fingers in a glove with the parallel legs of the sensor magnetically separated from one another by walls of the shield. Only the ends of the sensor legs are exposed through apertures through the shield for emergence of the various magnetic fields. The shield cancels unwanted fringing fields and better guides the magnetic fields in desired directions.

10 Claims, 4 Drawing Sheets

SHIELDED EDDY CURRENT SENSOR FOR ENHANCED SENSITIVITY

This is a continuation-in-part of Ser. No. 08/682,066 filed Jul. 16, 1996, and now abandoned.

GOVERNMENT CONTRACT

This invention was made with government support under subcontract F728960 of Prime Contract F33619-91-C-2118. The government has certain rights in this invention.

BACKGROUND OF THE INVENTION

This invention relates to eddy current sensors, and particularly to eddy current sensors used for measuring various parameters of moving, electrically conductive objects, e.g. turbine blades, impellers, etc.

Eddy current sensors are known and used in a variety of applications. The present invention was developed in connection with the design of gas turbines and is described in connection therewith. The inventive sensors, however, have utility in other applications.

U.S. Pat. No. 4,847,556 (Jul. 11, '89) and 4,967,153 (Oct. 30, '90) both to Langley, disclose eddy current sensors for detecting various parameters, e.g. blade tip clearance, speed and transit time, of rotating blades of turbomachinery. The detected information is used for monitoring the performance and condition of the machinery.

The eddy current sensors disclosed in the patents (the subject matter of which is incorporated herein by reference) comprise a generally U-shaped member including two parallel legs each comprising a permanent magnet joined by a transverse flux bridge. One magnet has its North pole adjoining the flux bridge, and the other magnet has its South pole adjoining the bridge. This arrangement produces a static magnetic field bridging the space between the free ends of the magnets and spreading radially away therefrom. Two separate coils, connected in series, are disposed one each around each of the two permanent magnets, and the two series connected coils are connected to a signal processing circuit.

In the absence of any moving electrically conductive object within the static magnetic field produced by the two magnets, the static field remains undisturbed and no voltages are produced in the magnet mounted coils. However, when an electrically conductive object, e.g., the rotating blade of a turbine, passes through the static field of the two magnets, eddy currents are generated within the conductive object. The eddy currents themselves generate magnetic fields, and as these eddy current produced magnetic fields interact with the permanent magnet field, disturbances occur in the permanent magnet field which induce signal voltages in the two series connected coils mounted on the permanent magnets. Analysis of the induced coil voltages, as described in the patents, provides various information about the moving object, e.g., the speed of the object, its minimum distance from the sensor and the time of its closest passage by the sensor. As described in the patents, such information is useful for monitoring the operating characteristics of turbomachinery.

The present invention provides eddy current sensors having utility for generating information similarly as in the aforecited patents but having certain advantages over the sensors disclosed in the above-cited patents. These advantages are described hereinafter.

SUMMARY OF THE INVENTION

An eddy current sensor according to a first embodiment of the invention, for use in relatively low temperature environments, comprises a generally E-shaped flux conducting structure including three parallel legs end-connected to a transverse flux bridge. A coil is mounted on each of the outer legs and equal currents (e.g., by connecting the coils in series) are caused to flow through the coils in such directions for generating two equal strength magnetic fields. Each field comprises continuous flux lines flowing through a respective outer leg, then to and through the central leg via the space between the legs, and thence back to the respective outer leg via the connecting flux bridge. Within the central leg, the flux lines from the two fields are oppositely directed, hence cancel one another. A separate, signal generating coil is mounted on the central leg and, in the absence of electrically conductive objects serving to disturb the symmetry of the two current induced fields, no signal is generated in the central coil. Conversely, when one of the two fields is disturbed separately from the other, a net field is generated within the central leg causing a signal voltage indicative of the nature of the disturbance.

Preferably, a.c. currents of a relatively high frequency, e.g. 1 MHz, are used for generating the two equal strength magnetic fields. Also, and particularly in connection with the use of a.c. driving currents, substantially all portions of the E-shaped member, excluding the outwardly facing end surfaces of the three legs, are preferably surrounded by magnetic shields, e.g., by an electrically conductive material such as copper, which serve to better guide the magnetic fields.

In a second embodiment of the invention, for use in relatively high temperature environments, the aforementioned E-shaped "flux conducting" structure is still present except that it is of a refractory material, e.g., ceramic, having a quite low magnetic permeability and having little flux conducting capability. In this embodiment, the aforementioned "preferably" used magnetic shields are essential for proper shaping and guiding of the sensor magnetic fields.

DESCRIPTION OF THE DRAWINGS

The drawing figures are schematic and not necessarily to scale.

DESCRIPTION OF PREFERRED EMBODIMENTS

Figure 1:
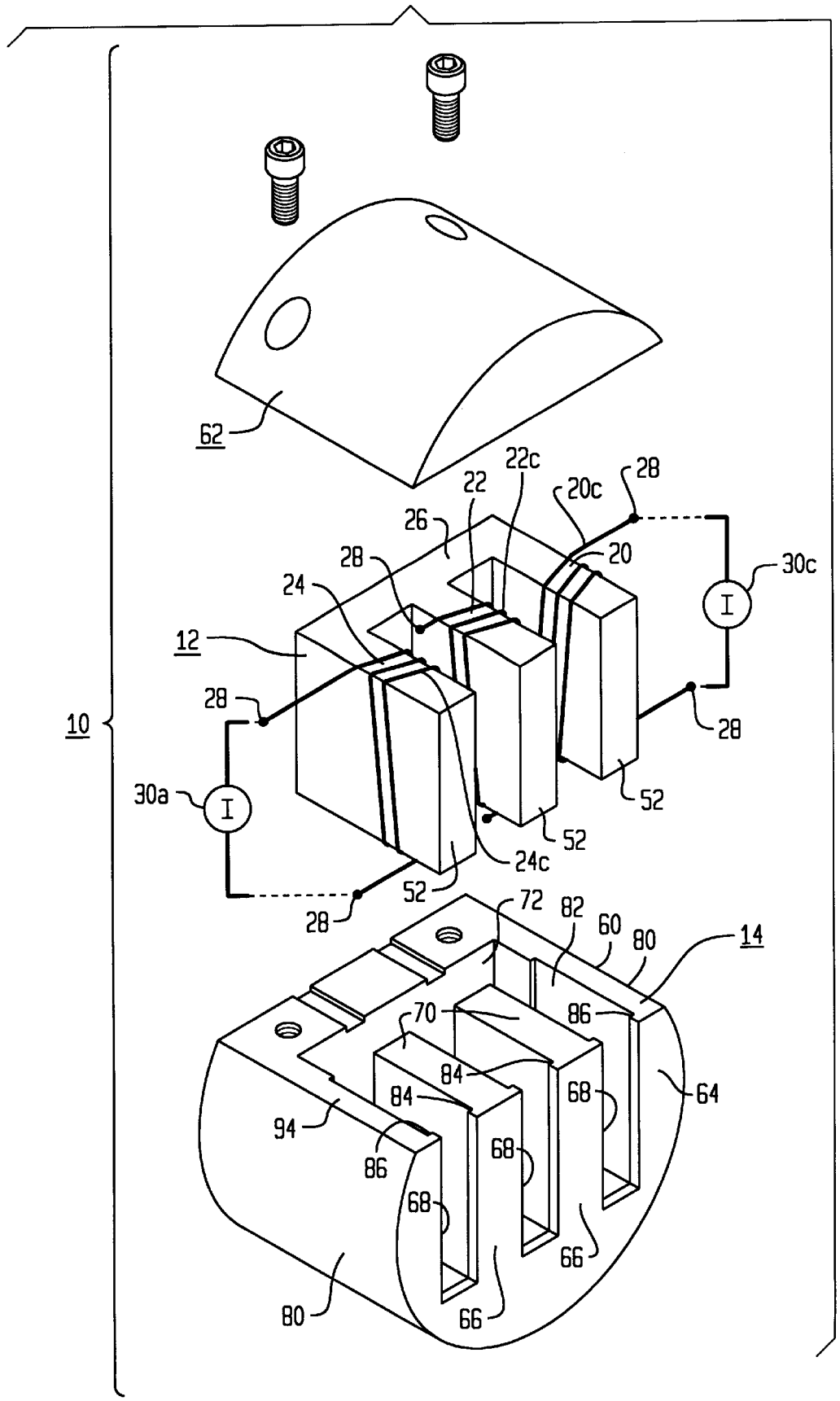
FIG. 1 is an exploded view, in perspective, of an eddy current sensor according to the present invention; the sensor including an E-shaped coil supporting member of, in a first embodiment of the invention, a high magnetic permeability material, and a substantially completely enclosing magnetic shielding member.

FIG. 1 shows, in perspective and exploded, a first embodiment of an eddy current sensor 10 in accordance with this invention. In this embodiment, the sensor comprises two portions; a magnetic, flux conducting and guiding core 12 and an optional (but generally preferred) shielding member 14 and 62. As discussed further hereinafter, the sensor 10 is intended for use at relatively "low temperatures", i.e., at temperatures below the Curie Point of the material of the core 12. At temperatures above the Curie Point, the magnetic permeability of the material is reduced to that of the surrounding air and the core 12 loses its flux guiding capability.

Flux conducting structures are well-known and the magnetic core 12 can be made using known technology and materials. The core 12 is preferably of a ferrite, i.e., one of a class of materials including iron oxide ($FeO_2$) and another material such as zinc, manganese, cobalt, magnesium or copper. A preferred ferrite uses manganese or zinc due to its low cost and good magnetic properties. The Curie Point of most practical magnetic material is generally less than 1,000° F.

The core 12 is generally of E-shape and includes three legs 20, 22 and 24 interconnected by a transverse bridge 26. The legs and bridge are all solid; specifically, they are not laminated as is common with other E-shaped flux carrying members used in transformers and inductors. The high intrinsic resistivity of ferrites obviates the need for laminations (i.e., eddy currents are highly suppressed within the material). The legs 20, 22 and 24 and the bridge 26 serve as conduits for magnetic flux, and the dimensions of the various portions of the core 12 are selected in accordance with known magnetic circuit concepts depending upon the device application.

An electrically conductive coil 20C, 22C and 24C, e.g., of insulated copper wire, is mounted on each of the legs 20, 22 and 24, respectively. The two coils 20C and 24C on the respective outer legs 20 and 24 are to conduct currents for generating magnetic fields, and each coil terminates in a pair of terminals 28 for connection to constant amplitude and frequency ac current sources of known type. For ease of illustration, two separate current sources 30a and 30c are shown. It is preferable, as hereinafter described, that the magnetic fields generated by the two coils be of identical strength but of opposite direction. One means of accomplishing this is to have the same current source supply the current flowing in coil windings 20C and 24C.

Figure 2:
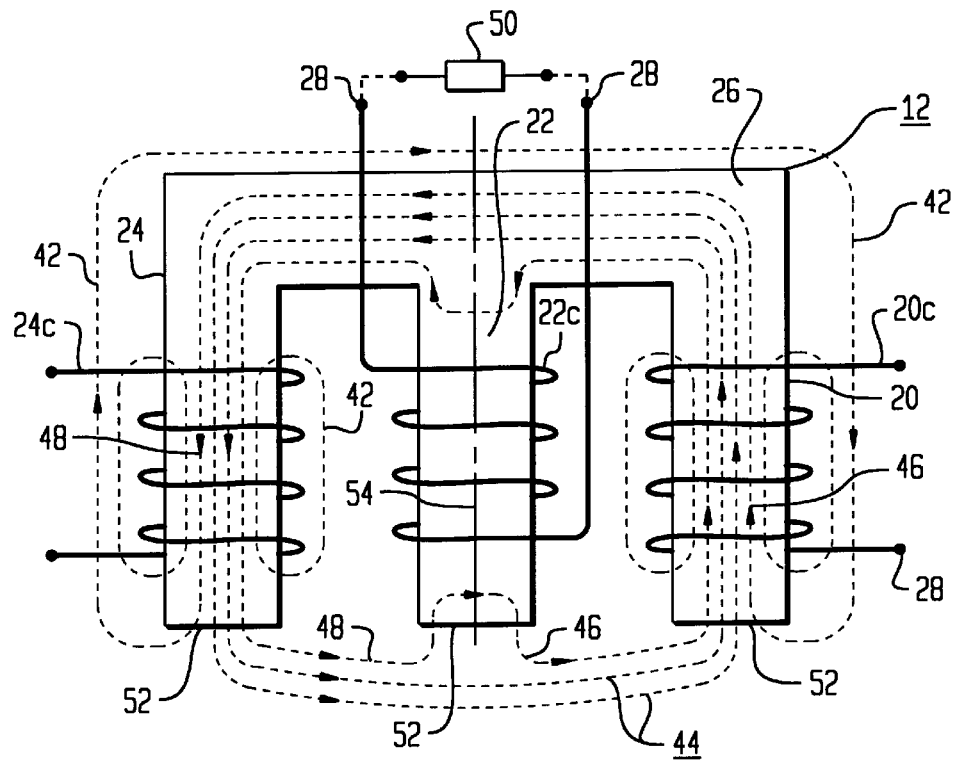
FIG. 2 is a plan view of the E-shaped member shown in FIG. 1 showing magnetic fields produced thereby in the absence of a shielding member.

FIG. 2 shows the magnetic fields generated by the core 12 when it is properly energized. The various magnetic fields are illustrated in conventional manner, i.e., by various closed loop flux lines with the density of the lines being indicative of the strength of the magnetic fields. In FIG. 2, the core 12 is not disposed within the shielding member 14 shown in FIG. 1, and various unwanted fringing fields (e.g., flux lines 42) are present in addition to the desired "sensing" magnetic field (e.g., flux lines 44).

When properly energized, the flux lines 46 and 48 through the respective outer legs 20 and 24 are always oppositely directed. Alternating currents (a.c.) are used for generating alternating direction magnetic fields, and in the instant illustrated in FIG. 2, the polarity of the magnetic fields is indicated by arrow heads on representative flux lines. Flux lines 46 and 48 from each field pass through the central leg 22 but always in opposite directions. Preferably, as mentioned, the strength of the fields produced by the two coils 20C and 24C are identical with the result that the two fields within the central leg 22 cancel one another.

Most simply, the two coils 20C and 24C are connected in series to a single current source; the two coils are identical, and the directions of windings of the two coils are selected to produce the desired relative field directions.

With the two fields through the central leg fully cancelling one another, no voltages are generated within the central leg coil 22C.

The central coil 22C is separate from the two outer coils 20C and 24C and serves as a signal generating means for sensing changes in the relative strengths of the two fields 46 and 48 passing through the central leg 22. The coil 22C has a pair of end terminals 28 for connection to a known signal detector 50, e.g., a synchronous demodulator.

As mentioned, the core 12 generates a "sensing" or desired magnetic field 44 along with various fringe fields 42. By way of word description, the sensing field is generally "arched" and "spreads outwardly" from "outwardly facing end surfaces" 52 of the three legs 20, 22 and 24. The core 12 is symmetrical about a central axis 54, and all the various flux loops shown in FIG. 2 lie mainly in the plane of the paper of FIG. 2. The core 12 has a depth dimension perpendicular to the plane of the paper but, owing to the symmetry of the core, the flux loop pattern shown in FIG. 2 represents the patterns in all sectional planes through the core parallel to the plane of the paper.

The sensing magnetic field 44 is used for obtaining "sensed" information, as hereinafter described, and the sensitivity of the sensor 10 is a function of the strength of the field 44. The various fringing fields 42, in this embodiment, serve no useful function, and the existence of these fields, generated by the same currents which produce the sensing field 44, reduce the strength of the field 44. One purpose of the shielding members 14 and 62 is to suppress the fringing fields for increasing the sensitivity of the sensor or for same sensitivity, reducing required current.

Figure 3:
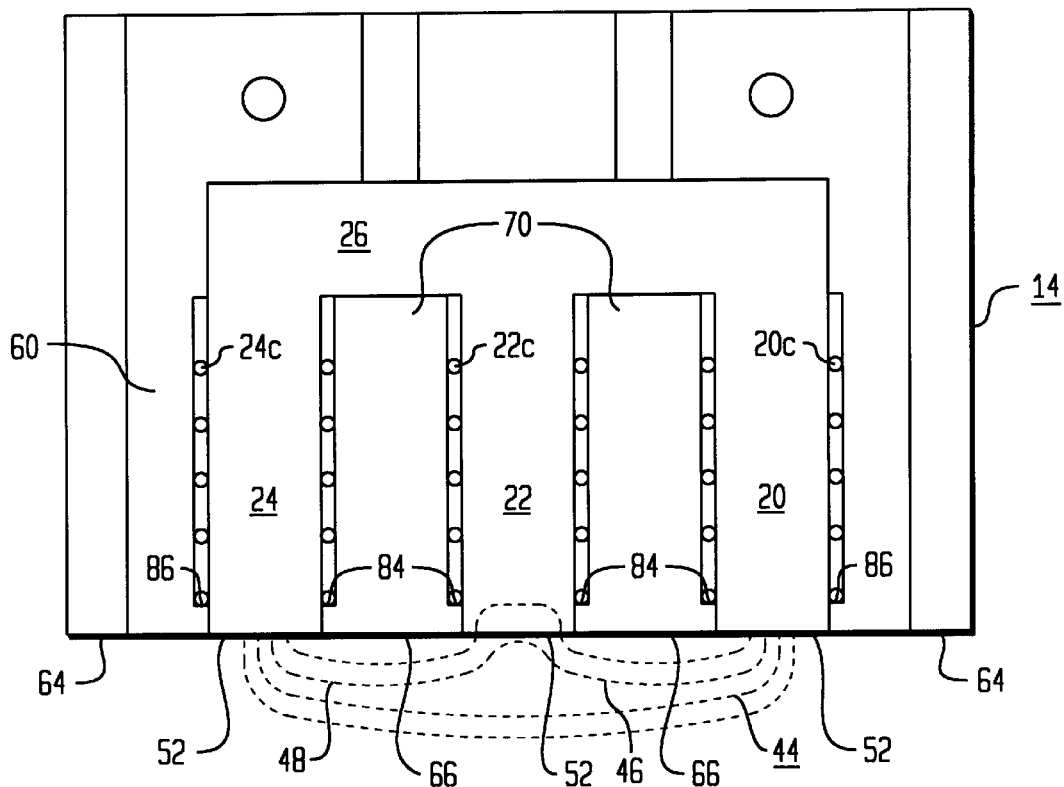
FIG. 3 is similar to FIG. 2 but showing the effect of disposing the E-shaped member within the shielding member shown in FIG. 1.

This is illustrated in FIG. 3 which is a plan view of the sensor shown in FIG. 1 with the core 12 disposed within the shielding member 14 but without the covering lid 62.

The shielding member 14 is of an electrically conductive material, e.g. copper. When disposed in closely surrounding relation with the core 12, and within the fringing fields of the core, eddy currents are generated within the conductive material of the shielding member by the alternating direction (time varying) magnetic fields. The eddy currents, in turn, generate magnetic fields which tend to cancel, hence suppress, the originating fields. In effect, flux loops from the sensing magnetic field are blocked from contributing to the fringing fields, hence rearrange themselves for better contribution to the strength of the useful sensing field. Although power is consumed for generating the eddy currents in the shielding member, the net result is a significant increase in the strength of the useful sensing field.

A further function of the shielding member is to serve as a housing for the entire sensor 10. To this end, it comprises (FIG. 1) a generally cup-shaped member 60 having a shaped recess for snug receipt of the E-shaped core 12 and a lid 62 for enclosing the core within the member 60. As mentioned, the shielding member 14 is of a time varying magnetic field blocking material and for propagation of the sensor sensing magnetic field 44 (FIG. 3), a "front " end 64 of the member 60 comprises two spaced apart columns 66 providing three openings 68 into the member 60. Parallel walls 70 extend inwardly of the member 60 from respective columns 66 and terminate in spaced apart relation from a solid, rear wall 72 of the member. The combination of the parallel, spaced apart inner walls 70, the rear wall 72, and side walls 80 of the member having inner surfaces 82 parallel to the inner walls 70 provide an E-shaped recess for snug fit of the E-shaped core 12.

The interior surfaces of the two columns 66 form corners or ledges 84 with the inwardly propagating walls 70. Similarly, corners 86 are provided where the side walls 80 join the front end of the member 60.

As described, and as illustrated in FIGS. 1, 2 and 3, a coil 20C, 22C and 24C is mounted on respective legs 20, 22 and 24 of the core 12. When the core 12 is disposed within the shielding member 14, each coil fits snugly within its respective recess portion with the outer sides of the coil engaged oppositely disposed wall surfaces of the member 60. The middle coil 22C, for example, engages facing surfaces of the two walls 70. The "front" end of each coil engages a respective corner or ledge 84 and 86 formed at an inside surface of the front end 64 of the member. This arrangement provides automatic positioning and alignment of the core 12 within the shielding member 14 upon pressing the core 12 inwardly of the member 60 through its open "top" end.

End terminals of the various coils are then led, e.g., via insulated wires, through openings through the rear wall 72 for external connections. For greater rigidity and reduction of vibrations, remaining spaces within the shielding member 14 are filled with a known electrically non-conductive and non-magnetic potting material.

Finally, to complete the sensor 10, the lid 62 is screwed onto the surface 94 of the member for completely enclosing the core 12 except for end faces 52 of the three legs 20, 22 and 24 which are exposed through the opening 68 formed by the two columns 66. In the present embodiment, the leg end faces 52 are substantially flush with the outer surfaces of the front end 64 of the member and form a portion of the external surface of the sensor 10.

A feature of the completed sensor 10 is that it can be quite small, e.g., having outside dimensions of 0.4 by 0.4 by 0.5 inches, and can be extremely rugged. In general, the sensor can be used similarly as known eddy current sensors and, more specifically, similarly as disclosed in the afore-cited patents to Langley.

Figure 4:
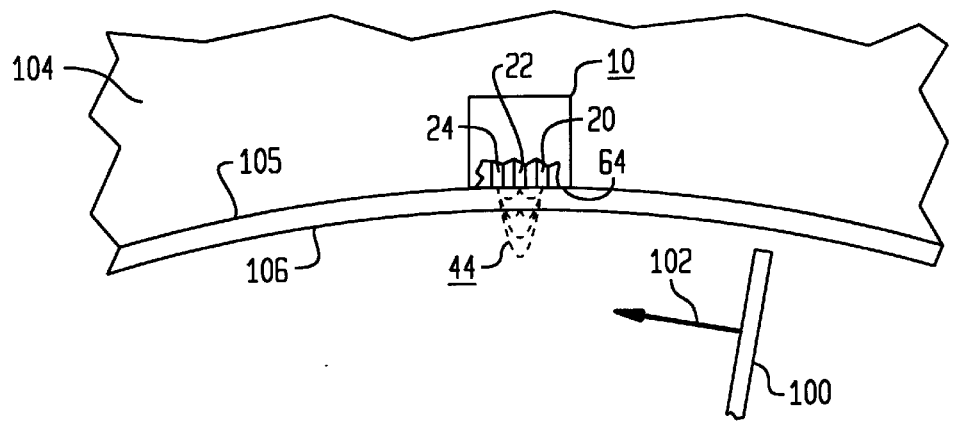
FIGS. 4–6 are schematic views showing one application of the eddy current sensor shown in FIG. 1.
Figure 5:
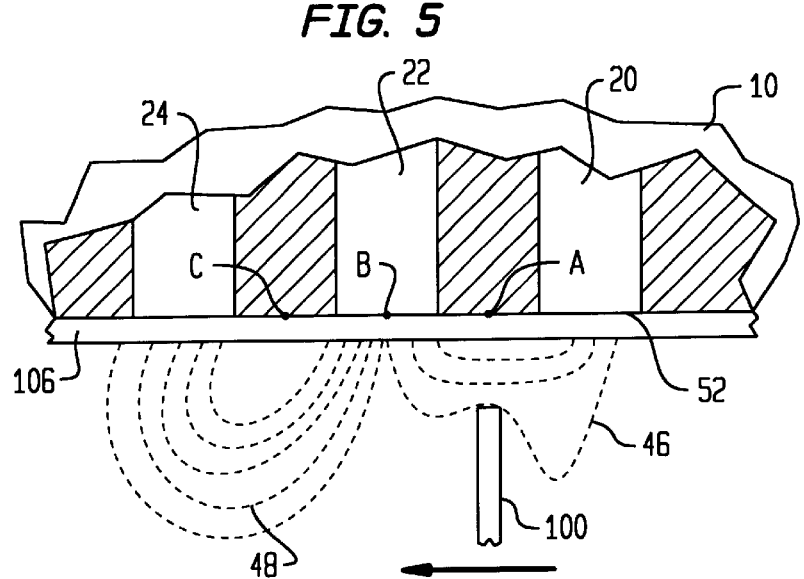
Figure 6:
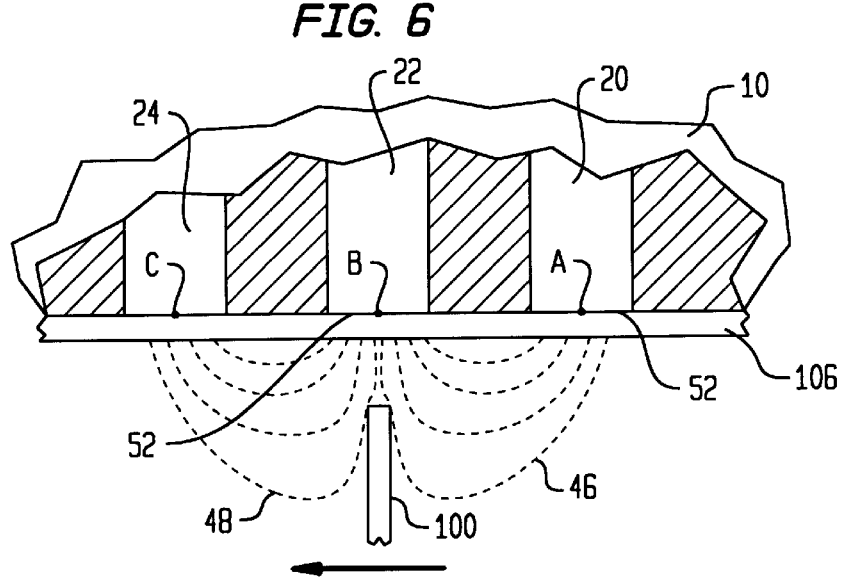

FIG. 4 shows an example of a use of the sensor, which use is generally similar to the Langley patent use. The illustrated use is within a gas turbine containing a turbine blade 100 of an electrically conductive material rotating about an axis (not shown) perpendicular to the plane of the page of FIG. 4 and moving in the direction of the arrow 102. The blade 100 is mounted within a housing wall 104 of the turbine and the sensor 10 is mounted and firmly secured within an opening in the housing wall. As illustrated, the front end 64 of the sensor 10 is flush with the interior surface 105 of the housing wall 104, and both the wall 104 and sensor are covered with a thin electrically non-conductive and non-magnetic material layer 106 normally used in gas turbines for preventing damage of the blade 100 owing to any accidental contact with the wall surface. The layer 106 is transparent to magnetic fields and the sensing magnetic field 44 of the sensor projects into the blade chamber and into the path of the moving blade 100. (In FIG. 4 and in FIGS. 5 and 6, forwardly facing end portions of the three legs 20, 22 and 24 of the core 12 are shown. The coils 20C, 22C and 24C mounted on the three legs are not shown.)

In FIG. 4, the blade 100 has not yet reached the vicinity of the sensor 10 and the sensing magnetic field 44 of the sensor is not yet disturbed by the blade. As previously described in connection with FIG. 2, the sensing field is made up of two separate fields generated by coils 20C and 24C mounted on respective outer legs 20 and 24 of the core 12. Both fields pass through the coil 22C on the central leg 22 but, being oppositely directed along the leg 22, fully cancel one another. Thus, no signal voltage is induced in the signal coil 22C.

As the blade approaches the sensor from the right-hand side as viewed in FIG. 4, the blade first enters (FIG. 5) the right-hand portion of the sensing magnetic field. The blade 100 is moving relative to the field 44 both because of the actual movement of the blade in the direction of the arrow 102 and because the magnetic field is an a.c. induced field. As discussed hereinafter, a preferred interaction between the blade 100 and the sensing field is due substantially only to the frequency of the magnetic field 44 and basically independent of the velocity of the blade due to the high frequency nature of the magnetic field 44 and the relatively low frequency passage of the blade 100.

The relative movement between the sensing field 44 and the blade 100 induces eddy currents within the blade which, as known, flow in directions for inducing magnetic fields which oppose the sensing field 44. The sensing field 44 is thus disturbed, but asymmetrically owing to off-center disposition of the blade relative to the field 44. Owing to such disturbance and attendant re-orientation of the flux lines of the sensing field caused by the presence of the blade, the distribution of flux lines within the central leg 22 changes resulting in the presence of a net field through the leg 22 and through the signal coil 22C mounted thereon. The net field is an a.c. field, hence induces a voltage in the signal coil 22C.

Figure 7:
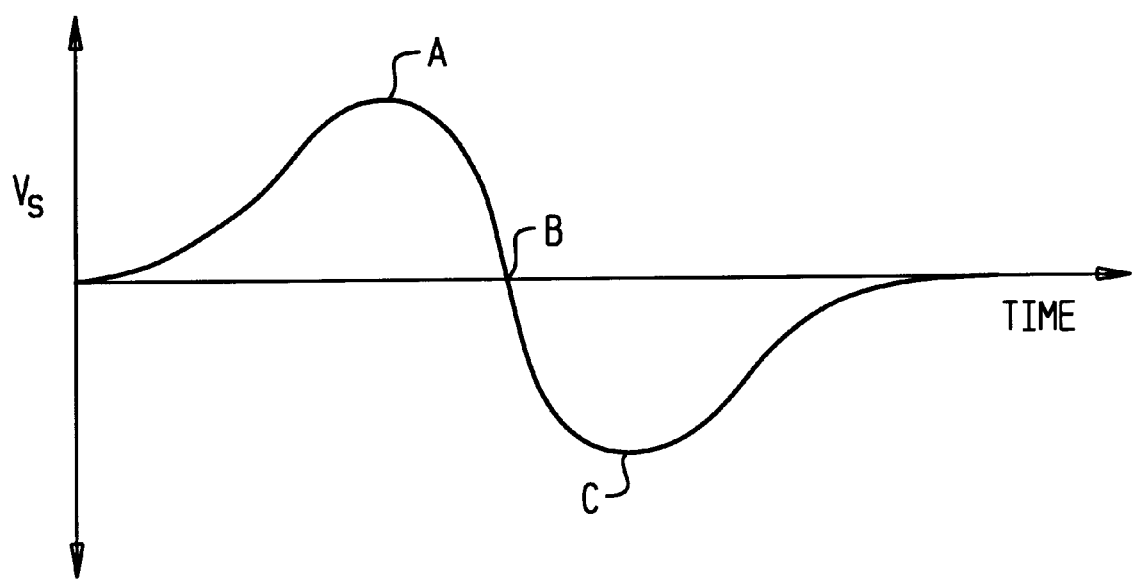
FIG. 7 is a graph, after simple signal processing, of the signal output of a sensor being used as illustrated in FIGS. 4–6.

The output signal of the sensor has a waveform such as shown in FIG. 7. The first amplitude peak A occurs when the tip of the blade is centered (FIG. 5) between the leg 20 and the leg 22 of the sensor. Such centered position is indicated by the point marked A in FIG. 5. At point A, the blade is minimizing the flux loops 46 of coil 20c while leaving the flux loops 48 of coil 24c unchanged, hence provides the maximum disturbance and unbalance of the field within the central coil 22C.

As the blade 100 continues to move to the left, and to a point B centered (FIG. 6) relative to the face 52 of the central leg 22, the blade interacts symmetrically with flux loops 46, 48 and with equal effects on the two fields passing through the central coil 22C. The fields are again equal (although of different value from the condition when no blade is present), the fields again cancel, and the output signal becomes zero. With further blade movement to the left (not illustrated), the flux loop 48 is increasingly disturbed while the flux loop 46 is decreasingly disturbed, and the output signal reaches a second peak C of opposite polarity when the blade is centered at a point C between the leg 22 and the leg 24.

The amplitude of the voltage signal produced in coil 22c indicates spacing between the blade tip and the sensor. As the blade passes the sensor, the elapse-time between points A and C of the signal is indicative of the speed of the blade. Additionally, differences in elapse time between point A and point B, and point B and point C are indicative of the vibrational state of the blade.

As mentioned, the sensor 10 may be used in applications similar to those of the sensor disclosed in the Langley patents. However, the inventive sensor possesses several significant advantages over the Langley sensor.

In sensors according to the invention, the magnetic fields produced by the coils 20c and 24c function to produce a null in the coil 22c in the absence of a disturbance. When a disturbance is introduced in the magnetic field of the central leg, a signal which varies about zero (the null condition) is produced. Producing a signal which varies about the null condition enables the production of a very sensitive condition even when the signal is very small. The inventive scheme avoids the need to subtract one signal from the other, where both signals may be large and the difference between the two signals is difficult to obtain.

The Langley sensor uses two permanent magnets whereas the inventive sensor uses two electromagnets (each comprising an outer leg 20 and 24 and the respective coils 20C and 24C mounted thereon). Permanent magnets suffer from two serious disadvantages, particularly when exposed to high temperature environments such as present within large power gas turbines, such as used in marine and aviation applications. One disadvantage is that permanent magnets tend to lose their magnetic properties when exposed to high temperatures and the other disadvantage is that the level of magnetism tends to change under temperature cycling conditions, e.g., when the turbine runs at different power levels including when it is turned on and off.

Because the amplitude of the output signal generated by an eddy current sensor is a function of the strength of the sensing magnetic field, changes in the strength of the field introduce errors in the output data from the sensors.

Electromagnets, however, such as used in the inventive sensors, do not experience such temperature dependence of the magnetic fields, and the inventive sensors are usable at extremely high temperatures (in comparison with permanent magnets) and are substantially totally unaffected by temperature changes or cycling. Obviously, the sensor must be designed to avoid catastrophic failure due to the melting of parts or the like.

Additionally, the ability to change the strength of the magnetic fields by simply changing the amplitude of the current offers design flexibility. For permanent magnetism, field strength can only be changed by changing the volume or shape of the permanent magnet.

While the inventive sensor can be used with d.c. currents (with equal and oppositely directed, and cancelling, static magnetic fields in the central leg 22), a much preferred use is with a.c. currents at a relatively high frequency, e.g., 1 MHz. By "relatively high" is meant that the rate of change of the magnetic field is far faster than the speed of movement of the conductive object being detected, with the result that the output signal is substantially independent of the speed of movement of the conductive object.

When a static magnetic field is used, such as in the Langley patent sensors, the relative movements between the conductive object and the magnetic flux lines necessary for the induction of eddy currents (essential for the operation of the sensors) is provided solely by the moving object. The amplitude of the output signal of the sensors is thus a function of several factors, namely, the speed of the conductive object, its distance (clearance) from the sensor, the conductivity of the object, and the sensing field strength. A principal use of eddy current sensors in turbomachinery is for monitoring changes in clearance caused by mechanical vibrations and parts wear. Such clearance variations are relatively quite small and can be completely masked by extremely small and difficult-to-detect variations in blade rotation rates.

At relatively high a.c. frequencies, however, the relative motion between the changing magnetic fields and the conductive object is so rapid as to be substantially independent of the rate of movement of the conductive object. In tests of the inventive sensor, for a given position (and spatial relationship between a blade tip and the sensor) substantially identical output signals (e.g., the amplitude thereof) are obtained both when the turbine blade is stationary (at points A or C in FIG. 5) and when the turbine is running at full speed (e.g., at a blade tip speed of 20,000 inches per second).

A further advantage of the use of varying magnetic fields is that far more effective shielding members are possible for reducing the amplitude of wasteful fringing fields. This was discussed previously in connection with FIGS. 2 and 3. As described, the attenuation of the fringing fields results from the generation of eddy currents in the surrounding electrically conductive shielding member. The generation of shielding member eddy currents requires time varying magnetic fields which are not present in the static field sensors of the Langley patents. Accordingly, effective shielding of the static fringing field associated with the Langley sensors is not practical and the Langley static field sensors are inherently inefficient.

Additionally, shielding also provides a high degree of noise reduction. Stray magnetic fields from other sources are highly attenuated dramatically reducing the noise floor of the sensor.

As mentioned, a driving current frequency of around 1 MHz is found satisfactory with the gas turbine tested. The actual frequency used is a function of the application of the sensor. In general, the higher the frequency, the more independent is the output signal voltage of the speed of movement of the conductive object being detected. Also, the higher the frequency, the thinner is the "skin" region of the conductive object in which the eddy currents are generated. The thinner the skin region, the less dependent is the output signal on the thickness or conductivity of the object being detected and on the thickness of the surrounding shielding members.

Additionally, the sensor being nearly purely inductive can be placed in series with a capacitor forming a resonant circuit. Tuning the capacitor or adjusting the frequency of the a.c. currents to create resonance dramatically reduces the current flowing from a current source without reducing the currents flowing in the coils 20C and 24C. The overall result is that the sensor requires very little power (e.g., less than one watt).

Heretofore, reference has been made to a.c. magnetic fields, that is, to alternating direction fields generated by alternating current. Eddy currents, however, are generated in response to any varying amplitude magnetic field such as can be produced by varying amplitude d.c. currents. The use of a.c. currents is a generally preferred approach, although varying d.c. currents may also be used.

A second embodiment of the invention is now described which, for example, can have the exact same appearance as the illustrated first embodiment.

The principal difference between the two embodiments is that, owing to the environment in which the second sensor is to be used, the E-shaped core 12, used for supporting the three cores 20C, 22C and 24C, has little or no flux conducting capability. For example, if the sensor according to the second embodiment is to be used at a temperature of around 2,000° F., which is well above the Curie Point of most practical magnetic materials, the preferred material of the core 12 is a refractory ceramic, e.g., alumina or berryllia. The magnetic permeability of such ceramics is quite low. In other applications, even at relatively low temperatures, other factors may prevent the use of high permeability materials in the core 12.

In these (second embodiment) applications, the core 12, of low magnetic permeability, is not effective for conducting magnetic flux lines and is not effective, as described in connection with the sensor 10, for shaping and guiding the magnetic fields produced by the coils 20C and 24C mounted on the outer legs 20 and 24 of the core 12. Indeed, with such a low permeability core 12, and without a shielding member 14 in place, the unwanted fringing fields (flux lines 42 in FIG. 2) would dominate and the desired sensing field (flux lines 44) would be nil.

Conversely, with the shield 14 in place, as the otherwise unwanted fringing field flux lines 42 start to penetrate into the shield, eddy currents are generated within the conductive material of the shield. These eddy currents generate magnetic fields which oppose the flux lines 42 and, in effect, prevent the penetration of the flux lines into and through the shield. Because all flux lines must form closed loops, the flux lines 42 are forced to travel along the walls of the shield and to eventually pass out of the shield through (FIG. 1) the shield apertures 68.

Outside the shield, the redirected flux lines 42 merge with the sensing field flux lines 44 and reenter the shield 14 (to complete their closed loop paths) through the shield central aperture 68 where they interact with the sensing coil 22C. In effect, the walls of the shielding member 14 serve as flux "mirrors" for reflecting the otherwise undesired fringing flux lines 42 and guiding these flux lines for contribution to the desired sensing magnetic field 44.

Accordingly, in this second embodiment, i.e., where the coil supporting core 12 is of low magnetic permeability (for whatever reason), the presence of the shielding member 14 is essential for guiding and shaping the magnetic sensing field. Of course, the lack of a flux conducting capability in the coil supporting core 12 reduces the sensitivity of the sensor due to the increased reluctance seen by the flux. The loss in sensor sensitivity can be made up by increasing the current in the two sensor drive coils 20C and 24C.

What is claimed is:

1. An eddy current sensor comprising first and second electrical coils each for generating respective first and second magnetic fields in response to the flow of electrical currents through said coils, and a third electrical coil for generating a signal voltage in response to a variable magnetic field intersecting said third coil, said coils being arranged relative to one another whereby said first and second fields combine to form a third magnetic field having a first portion forming a sensing field extending from an end of the sensor and having a second portion intersecting said third coil, whereby, upon disturbance of said sensing field by an electrically conductive object therewithin, said disturbance is detected by said third coil, the sensor including an eddy current suppressing frame on which all of said coils are mounted for defining paths through said frame for said magnetic fields, and further including a shielding member of electrically conductive material substantially fully enclosing and magnetically isolating said frame and said coils from one another along paths other than through said frame with the exception of said end of said sensor exposed through said shielding member for directing said coil generated magnetic fields towards said sensor end for amplifying said sensing field.

2. A sensor according to claim 1 wherein said frame has a generally E-shape including three generally parallel and spaced apart legs end connected to a common bridge, one of said legs being disposed between the other two of said legs, said first and second coils being mounted on respective ones of said other two legs, and said third coil being mounted on said one leg.

3. A sensor according to claim 2 wherein said frame is of a refractory, non-magnetic material.

4. A sensor according to claim 3 wherein said frame is of a ceramic material.

5. A method of operating an eddy current sensor comprising first, second and third electrical coils mounted in spaced apart relation on a support member, the method comprising the steps of flowing variable amplitude currents through said first and second coils for generating first and second variable amplitude magnetic fields which combine to form a variable amplitude sensing magnetic field having two portions, a first of which extends away from one end of said sensor and the second of which intersects said third coil, and disposing the sensor in an eddy current generating housing, of electrically conductive material substantially fully enclosing all but said one end of the sensor which is exposed through an opening in said housing for directing said coil generated fields towards said sensor end for increasing the strength of said sensing magnetic field.

6. A method according to claim 5 including causing a.c. currents at a frequency of at least 1 mHz to flow through said first and second coils.

7. A method according to claim 5 including causing said currents to flow through said coils of such magnitude and direction for generating equal strength first and second fields of opposite magnetic polarities for causing said second portion to have substantially zero strength.

8. A method according to claim 5 wherein the sensor comprises a frame having a generally E-shape including three generally parallel and spaced apart legs end connected to a common bridge, one of said legs being disposed between the other two of said legs, said first and second coils being mounted on respective ones of said other two legs, said third coil being mounted on said one leg, and disposing the sensor in said housing such that portions of the housing substantially fully enclose each of said legs, the spaces between said legs and said bridge and with the housing exposing end surfaces of said legs facing away from said bridge, said exposed end surfaces comprising said one end of the sensor.

9. A method according to claim 5, including the step of disposing the sensor in a wall of a turbine for sensing variable clearances between said wall and turbine blades passing said wall.

10. A housing for an eddy current sensor of generally E-shape including three generally parallel legs end-connected to a common bridge, one of said legs being disposed between the other two of said legs each of which mounts thereon a magnetic field generating first electrical coil, and a magnetic field sensing second electrical coil mounted on said one leg, the housing comprising a hollow shell of electrically conductive material for generating magnetic-field inducing eddy currents in response to variable amplitude magnetic fields, said shell including walls defining an E-shaped interior space including three generally parallel first spaces end-connected to a common transversely extending second space, each of said spaces being substantially completely enclosed by said shell except for openings through said shell at ends of said first spaces oppositely disposed to said second space, said space ends being each shaped in conformity with respective end surfaces of the three parallel legs of a said E-shaped sensor disposed within said shell with the parallel legs of the sensor disposed within respective parallel first spaces of said shell, each of said sensor legs being substantially fully enclosed and magnetically separated from the other sensor legs by walls of said shell except for said end surfaces of said legs exposed through said shell openings for allowing interaction of magnetic fields generated by said first coils with said enclosing shell walls for directing said magnetic fields through said shell openings.

* * * * *